(12) United States Patent
Eren et al.

(10) Patent No.: US 9,339,175 B2
(45) Date of Patent: May 17, 2016

(54) SYSTEM AND METHOD TO IMPROVE MOUTH DISEASE DIAGNOSIS

(75) Inventors: Selcuk S. Eren, Chapel Hill, NC (US); Brian J. Jaeger, Raleigh, NC (US); Douglas A. Law, Chapel Hill, NC (US); Paul A. Roberts, Raleigh, NC (US); Shawn K. Sremaniak, Raleigh, NC (US)

(73) Assignee: International Business Machines Corporation, Armonk, NY (US)

( * ) Notice: Subject to any disclaimer, the term of this patent is extended or adjusted under 35 U.S.C. 154(b) by 1396 days.

(21) Appl. No.: 11/967,620

(22) Filed: Dec. 31, 2007

(65) Prior Publication Data
US 2009/0167848 A1    Jul. 2, 2009

(51) Int. Cl.
| A61B 1/32 | (2006.01) |
| A61B 1/00 | (2006.01) |
| A61B 1/24 | (2006.01) |
| A61B 5/00 | (2006.01) |

(52) U.S. Cl.
CPC .............. *A61B 1/32* (2013.01); *A61B 1/00147* (2013.01); *A61B 1/24* (2013.01); *A61B 5/682* (2013.01)

(58) Field of Classification Search
CPC ....... A61B 1/00147; A61B 1/24; A61B 1/247
USPC ........................................ 348/66; 433/29, 31
See application file for complete search history.

(56) References Cited

U.S. PATENT DOCUMENTS

| 1,238,001 A * | 8/1917 | Cameron | 600/240 |
| 2,220,674 A * | 11/1940 | Bloomheart | 600/238 |
| 6,386,867 B1 * | 5/2002 | Durbin | A61C 9/00 433/214 |
| 6,714,657 B1 * | 3/2004 | Jacobs | A61B 1/247 382/100 |
| 7,540,647 B2 * | 6/2009 | Lee | A61B 1/05 348/66 |
| 8,376,743 B1 * | 2/2013 | Bukhary | A61B 1/24 128/859 |
| 2001/0010538 A1 * | 8/2001 | Ooshima | A61B 1/24 348/66 |
| 2002/0022211 A1 * | 2/2002 | Horiguchi | A61C 5/14 433/140 |

(Continued)

OTHER PUBLICATIONS

Wilder-Smith, Petra et al. "In vivo Imaging of Oral Mucositis in an Animal Model Using Optical Coherence Tomography and Optical Doppler Tomography" Apr. 16, 2007. Clinical Cancer Research 2007;13:2449-2454. pp. 1-7.*

(Continued)

*Primary Examiner* — Imad Hussain
(74) *Attorney, Agent, or Firm* — Steven M. Greenberg, Esq.; CRGO Law

(57) ABSTRACT

Embodiments of the present invention address the deficiencies of the art in respect to oral cavity medical assessment and provide a method, system and apparatus for mouth disease diagnosis and treatment. In an embodiment of the invention, an apparatus for scanning an oral cavity can include a mouth guard spreader that has a partially transparent receiving member that defines a receiving cavity, a first spreader portion and a second spreader portion coupled to the partially transparent receiving member. The apparatus further can include an image capture device for capturing images of the oral cavity disposed within the partially transparent receiving member of the mouth guard spreader. The apparatus yet further can include a storage device coupled to the image capture device for storing each captured image of the oral cavity.

12 Claims, 3 Drawing Sheets

(56) References Cited

U.S. PATENT DOCUMENTS

| | | | |
|---|---|---|---|
| 2003/0049585 A1* | 3/2003 | Severance | A61C 19/10 433/29 |
| 2003/0148243 A1* | 8/2003 | Kerschbaumer | A61B 1/00041 433/29 |
| 2005/0197529 A1* | 9/2005 | Hoshihara | A61B 1/00154 600/114 |
| 2006/0096602 A1* | 5/2006 | Brown | 128/861 |
| 2007/0068535 A1* | 3/2007 | Colman | A61B 1/00154 128/859 |
| 2007/0156028 A1* | 7/2007 | Van Lue | A61B 1/24 600/237 |
| 2008/0064001 A1* | 3/2008 | Dorfman | A61C 5/14 433/29 |

OTHER PUBLICATIONS

Zerbe, Melissa B. et al. "Relationships between oral mucositis and treatment variables in bone marrow transplant patients" 1992. Cancer Nusring 15(3):196-205, 1992. pp. 1-10.*

* cited by examiner

SYSTEM AND METHOD TO IMPROVE MOUTH DISEASE DIAGNOSIS

BACKGROUND OF THE INVENTION

1. Statement of the Technical Field

The present invention relates to systems and methods for assessing oral cavities and more particularly to an assessment process for oral mucosal damage caused by high dose chemotherapy/radiotherapy post treatments.

2. Description of the Related Art

In the medical field, emphasis is currently being placed on improving medical diagnosis while, at the same time, decreasing the cost for the examinations. For various conditions, the progress of a particular treatment is monitored and assessed on a regular basis to determine the effectiveness of that treatment. Typically, assessments of a given treatment will require hospital visits since these assessments are performed by specialists via visual inspection, and as such, the cost for monitoring the patients is significant. For example, one side effect of high dose chemotherapy/radiotherapy is oral mucosal damage. In as few as 12 hours after a high dose chemotherapy/radiotherapy treatment, symptoms of oral mucositis can be observed in a patient.

Oral mucositis is a painful problem that can affect the consumption of food and liquids by the high dose chemotherapy/radiotherapy patient. Treatments to reduce the oral mucositis are available; however, as previously mentioned, regular assessments are required to identify the best treatment. Typically, there are eight areas that should be evaluated in patient's mouth, which are (1) upper labial mucosa (e.g., upper lip), (2) mandibular labial mucosa (e.g., lower lip), (3) right buccal mucosa (e.g., right cheek), (4) left buccal mucosa (e.g., left cheek), (5) right lateral and ventral tongue, (6) left lateral and ventral tongue, (5) floor of the mouth and (8) soft palate.

SUMMARY OF THE INVENTION

Embodiments of the present invention address the deficiencies of the art in respect to oral cavity assessment and provide a novel and non-obvious method, system and apparatus for mouth disease diagnosis and treatment. In an embodiment of the invention, an apparatus for scanning an oral cavity can be provided. The apparatus can include a mouth guard spreader that has a partially transparent receiving member that defines a receiving cavity, a first spreader portion and a second spreader portion coupled to the partially transparent receiving member. The apparatus further can include an image capture device for capturing images of the oral cavity, which is disposed within the partially transparent receiving member of the mouth guard spreader. The apparatus yet further can include a storage device coupled to the image capture device for storing each captured image of the oral cavity.

In one aspect of the embodiment, the apparatus further can include a processor in communication with the image capture device and a monitor in communication with the processor for displaying one or more captured images.

In another embodiment, a method for mouth disease diagnosis and treatment can be provided. The method can include placing an image capture device into a mouth guard spreader to assemble an apparatus for scanning an oral cavity, strategically positioning the assembled apparatus into the mouth of a patient to create a small space between an interior portion of a cheek and an exterior gumline of the patient, capturing an image of the interior portion of the cheek, comparing the captured image to a previously captured image of substantially the same interior portion of the cheek to assess the progression of the mouth disease and determining a course of treatment based on the assessed progression of the mouth disease.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Embodiments of the present invention provide a method, system and computer program product for mouth disease diagnosis and treatment. In an embodiment of the invention, an apparatus for scanning an oral cavity can be provided. The apparatus can include a mouth guard spreader that has a partially transparent receiving member that defines a receiving cavity, a first spreader member and a second spreader member coupled to the partially transparent receiving member. The apparatus can include an image capture device, e.g., a video camera, for capturing images of the oral cavity that can be disposed within the partially transparent receiving member of the mouth guard spreader. The apparatus yet further can include a storage device coupled to the image capture device for storing each captured image of the oral cavity. In another embodiment of the invention, a method for mouth disease diagnosis and treatment can be provided. The method can include assembling an image capture device, e.g., a video camera, with a mouth guard spreader and strategically positioning the assembled apparatus into the mouth of a patient to create a small space between an interior portion of a cheek, e.g. the left or right buccal mucosa areas and an exterior gumline of the patient. An image of the cheek area and an exterior gumline can be captured. Thereafter, the captured image can be compared to a previously (or subsequently) captured image of substantially the same cheek area to assess the progression of the mouth disease or its treatment and determine a further course of action.

Figure 1A:
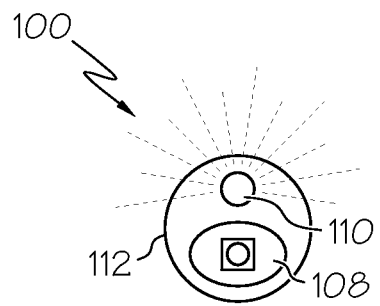
FIG. 1A is a top view of a schematic representation of an image capture device utilized in an apparatus for scanning an oral cavity.
Figure 1B:
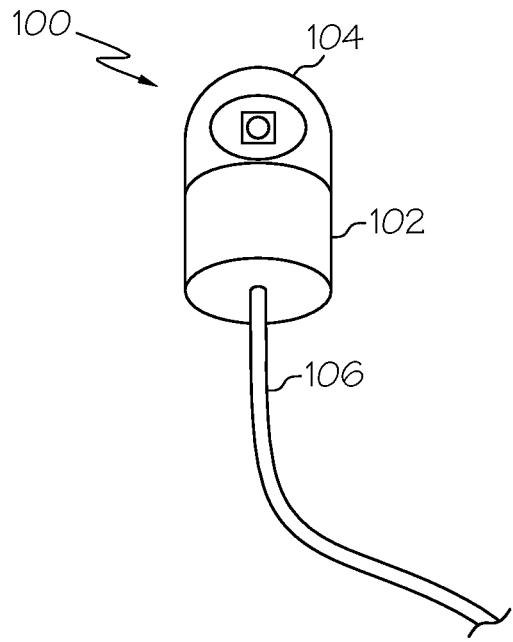
FIG. 1B is a side view of a schematic representation of an image capture device utilized in an apparatus for scanning an oral cavity.

In illustration, FIGS. 1A and 1B illustrate an image capture device utilized in an apparatus for scanning an oral cavity. The image capture device 100 can include a base portion 102 coupled to a top portion 104 and an electrical cord 106. The top portion 104 of image capture device 100 can include a camera 108 with a wide area lens, such as a "fish eye" lens, a light source 110, e.g., a light emitting diode (LED) and a camera dome 112 that includes at least a portion that is transparent coupled to the base portion 102. In one embodiment, the image capture device 100 captures an image of the oral cavity, e.g., the mouth of the patient, with the camera 108 and stores it in a storage device housed in the camera for later use. Alternatively, the electrical cord 106 can connect the camera 108 to an electronic storage device, such as a compact disk (CD), a digital versatile disk (DVD), a computer hard drive, a flash card, a smart card and an electronic diskette.

Figure 2:
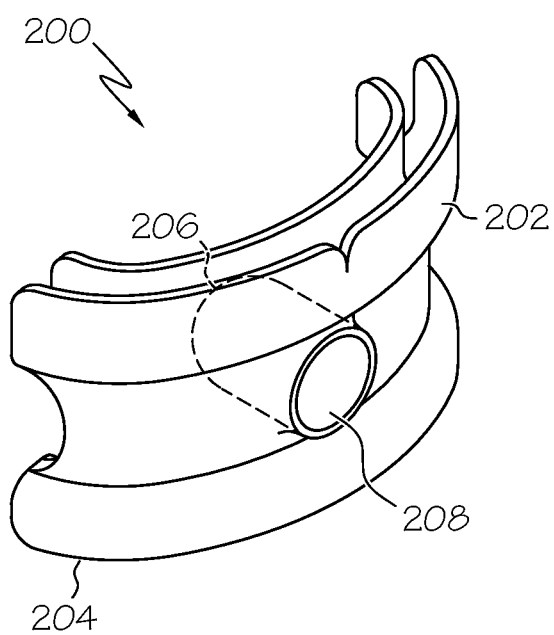
FIG. 2 is a perspective view of a schematic representation of an mouth guard spreader utilized in an apparatus for scanning an oral cavity.

In further illustration, FIG. 2 is a schematic representation of a mouth guard spreader utilized in an apparatus for scanning an oral cavity. The mouth guard spreader 200 can include a partially transparent receiving member 206 that defines a receiving cavity 208, a first spreader member 202 and a second spreader member 204 coupled to the partially transparent receiving member 206. In this embodiment, the first spreader member 202 and the second spreader member 204 are configured such that a patient can bite down on the mouth guard spreader 200 to secure the mouth guard spreader 200 to the front portion of the mouth of the patient. From this location, a medical practitioner can capture images of the interior and back of the mouth and store them in a data store for analysis or later retrieval. In other embodiments of the mouth guard spreader 200, the first spreader member 202 and the second spreader member 204 can have other configurations, such as set of tubular or relatively flat prongs, to capture images of the exterior of the gumline and the cheek areas of the mouth and discussed in greater detail with reference to FIGS. 4A and 4B.

The mouth guard spreader 200 can be made of rubber, plastic, or any other suitable materials known to those of ordinary skill in the art that are safe for use in the mouth of the patient. The mouth guard spreader 200 should be substantially rigid so as to assist in protecting the image capture device 100.

Figure 3A:
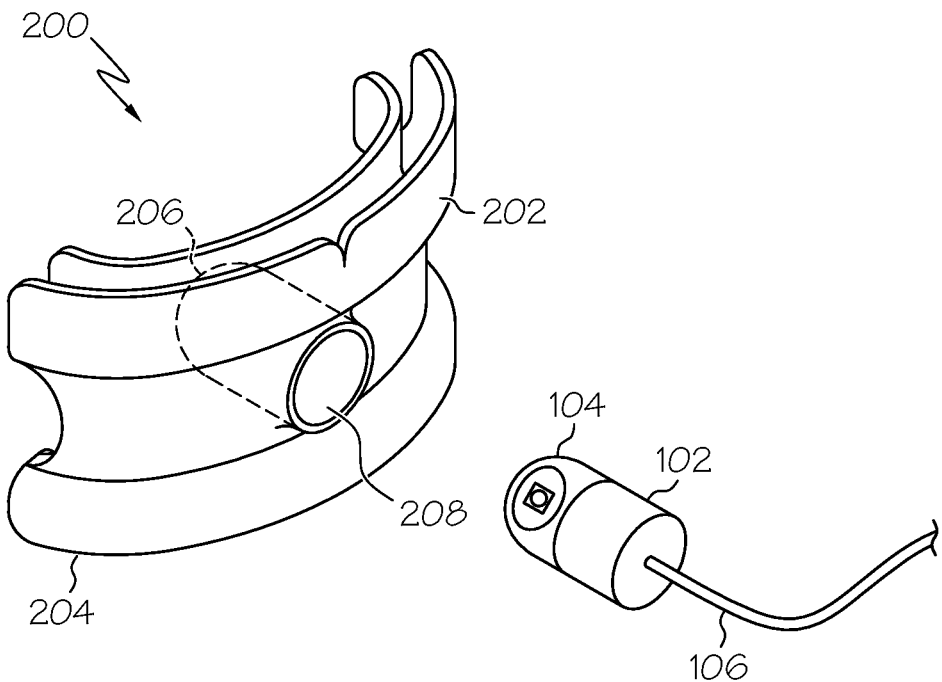
FIG. 3A is an exploded view schematic illustration of the apparatus for scanning an oral cavity.
Figure 3B:
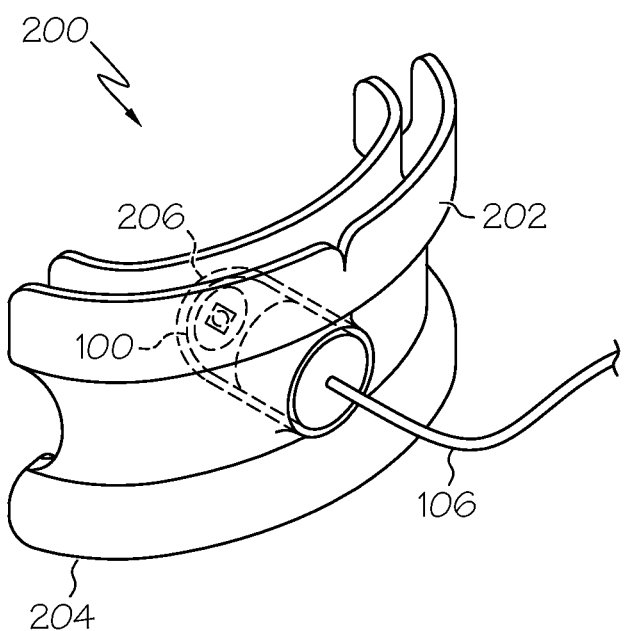
FIG. 3B is a schematic illustration of the apparatus for scanning an oral cavity.

In further illustration, FIGS. 3A and 3B are schematic illustrations of the apparatus for scanning an oral cavity. The apparatus for scanning an oral cavity can include the mouth guard spreader 200 and the image capture device 100. FIG. 3A illustrates an exploded view of the apparatus for scanning an oral cavity and in particular the alignment of the image capture device 100 to the receiving cavity 208 of the transparent receiving member 206 of the mouth guard spreader 200. FIG. 3B in turn illustrates the joining of the image capture device 100 to the receiving cavity 208 of the transparent receiving member 206 as the base 102 "snaps" into the transparent receiving member 206.

Figure 4A:
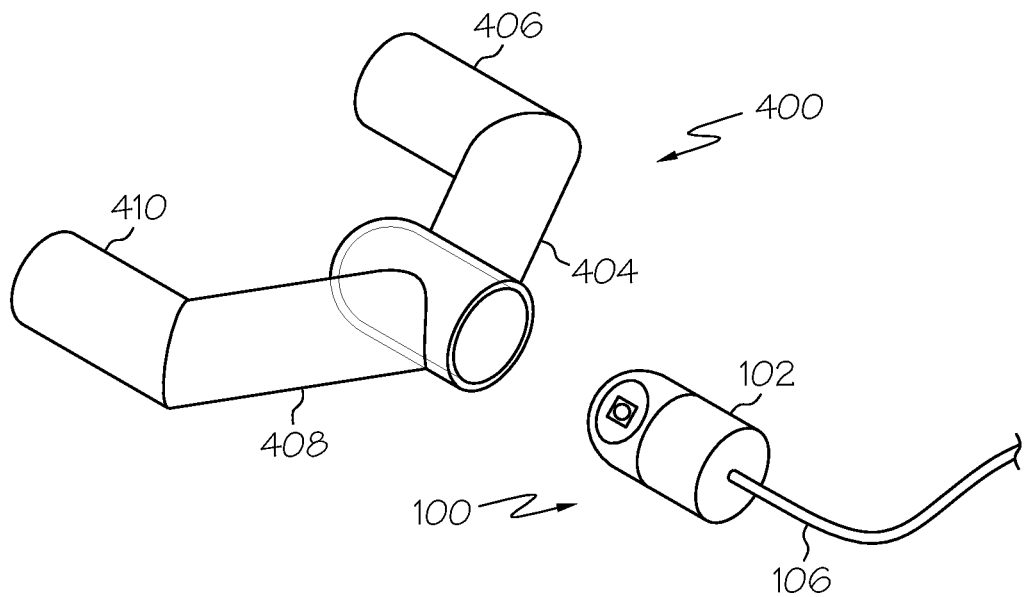
FIG. 4A is an exploded view schematic illustration of an alternate embodiment of the apparatus for scanning an oral cavity; and, FIG. 4B is a schematic illustration of the apparatus for scanning an oral cavity of FIG. 4A deployed in an oral environment.

In yet further illustration, FIG. 4A is an exploded view schematic illustration of an alternate embodiment of the apparatus for scanning an oral cavity. In this embodiment, the apparatus for scanning an oral cavity can include the mouth guard spreader 400 and the image capture device 100. The mouth guard spreader 400 is similar to the mouth guard spreader 200 of FIG. 2A and each can be interchanged with the other. As shown in FIG. 4A, the first spreader member of mouth guard spreader 400 can be a prong that can include a first angled prong segment 404 coupled to a partially transparent receiving member 402 that defines a receiving cavity 403 and a first extending prong segment 406 that is coupled to the first angled prong segment 404. The second spreader member of mouth guard spreader 400 also can be a prong that can include a second angled prong segment 408 coupled to the partially transparent receiving member 402 and a second extending prong segment 410 that is coupled to the second angled prong segment 408. Although the prongs are illustrated to be substantially tubular in FIG. 4A, the prongs also can be substantially flat and have a thickness in the range of approximately ¼ inches to 2 inches.

Figure 4B:
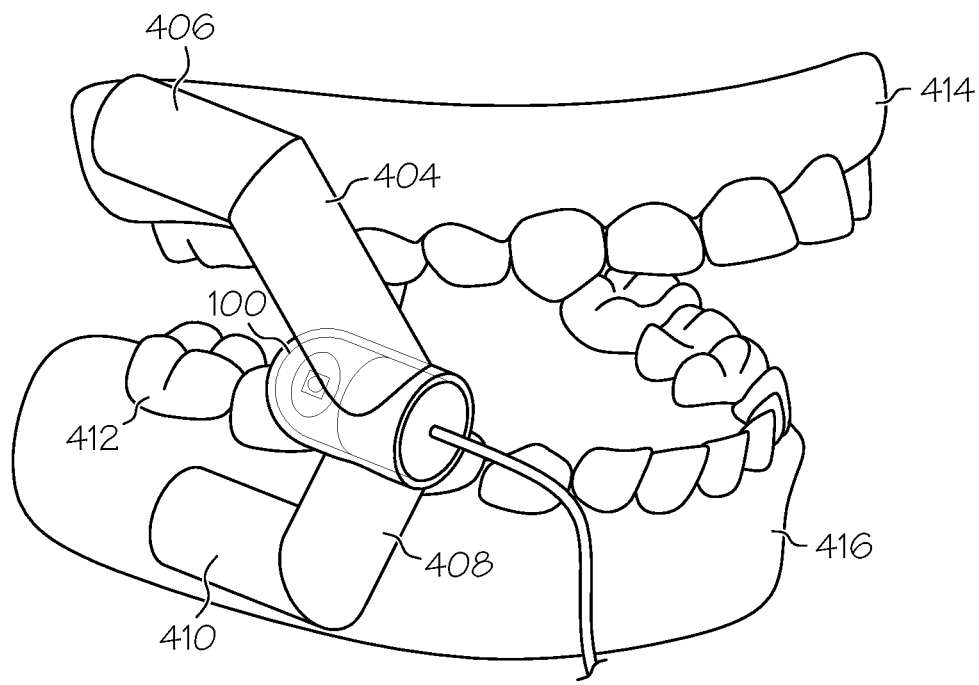

In still yet further illustration, FIG. 4B is a schematic illustration of an alternate embodiment of the apparatus for scanning an oral cavity of FIG. 4A deployed in the mouth of a patient. In use, a process for mouth disease diagnosis and treatment can include placing the a video camera 100 into a mouth guard spreader 400 to assemble the apparatus for scanning an oral cavity, strategically positioning the assembled apparatus into the mouth of a patient to create a small space between a cheek, e.g. the left or right buccal mucosa areas, and an exterior gumline of the patient. For example, the first prong of mouth guard spreader 400 can be positioned along the upper gumline 414 and the second prong of the mouth guard spreader 400 can be positioned along the lower gumline 416 to create a small space or gap between the right cheek and the upper and lower gumlines 414, 416, respectively. An image of the left cheek area and the exterior gumlines can be captured. Thereafter, the captured image can be compared to a previously captured image of the same cheek area to assess the progression of the mouth disease or its treatment and determine a further course of action. Additional images of substantially the same left cheek area and exterior gumlines can be captured over time. Using an image from a subsequent assessment, a medical professional or a processor can compare the mucositis color and size of the captured image to the mucositis color and size of a prior image to determine whether these factors have changed. Based on the progression or healing of the mucositis, the medical professional (or processor) can provide a course of treatment and/or medication.

The present invention can be realized in hardware, software, or a combination of hardware and software. An implementation of the method and system of the present invention can be realized in a centralized fashion in one computer system or in a distributed fashion where different elements are spread across several interconnected computer systems. Any kind of computer system, or other apparatus adapted for carrying out the methods described herein, is suited to perform the functions described herein.

A typical combination of hardware and software could be a general-purpose computer system with a computer program that, when being loaded and executed, controls the computer system such that it carries out the methods described herein. The present invention can also be embedded in a computer program product, which comprises all the features enabling the implementation of the methods described herein, and which, when loaded in a computer system is able to carry out these methods.

Embodiments of the invention can take the form of an entirely hardware embodiment, an entirely software embodiment or an embodiment containing both hardware and software elements. In a preferred embodiment, the invention is implemented in software, which includes but is not limited to firmware, resident software, microcode, and the like. Furthermore, the invention can take the form of a computer program product accessible from a computer-usable or computer-readable medium providing program code for use by or in connection with a computer or any instruction execution system.

We claim:

1. An apparatus for scanning an oral cavity, the apparatus comprising:
   a mouth spreader comprising opposing first and second angular spreader members coupled to one another at a receiving member, the opposing first and second angular spreader members acting in concert to create a gap between a cheek and a gumline of an oral cavity of only a single left or right side of a face by a first one of the spreader members contacting the cheek and gumline of the single side of a face to separate the cheek from the gumline and by a second one of the spreader members contacting only the cheek and gumline of the single left or right side of the face to separate the cheek from the gumline;
   an image capture device configured to capture images of an oral cavity and disposed within the receiving member; and,
   a data store coupled to the image capture device storing captured image of the oral cavity.

2. The apparatus of claim 1, wherein the first spreader member and the second spreader member are a first prong and a second prong.

3. The apparatus of claim 2, wherein the first prong is configured to include a first angled prong segment and a first extending prong segment and the second prong is configured to include a second angled prong segment and a second extending prong segment.

4. The apparatus of claim 2, wherein the first prong and the second prong have a substantially flat geometry.

5. The apparatus of claim 1, wherein the data store is one of a compact disk (CD), a digital versatile disk (DVD), a flash card, a smart card and an electronic diskette.

6. The apparatus of claim 1, wherein the image capture device is a camera having a wide angle lens.

7. The apparatus of claim 1, further comprising a processor for analyzing the captured image.

8. The apparatus of claim 1, further comprising a monitor for displaying the captured image.

9. The apparatus of claim 1, wherein the receiving member is partially transparent.

10. The apparatus of claim 1, wherein the first and second members and the receiving member are one piece.

11. The apparatus of claim 1, wherein the first and second members each define at an outer edge opposite the receiving member a channel into which teeth are placed.

12. The apparatus of claim 1, wherein the image capture device is tubular in shape and the receiving member also is tubular in shape and adapted to receive the image capture device.

* * * * *